United States Patent [19]

Abe

[11] 4,366,804
[45] Jan. 4, 1983

[54] WARMING DEVICE FOR GENERATING HEAT BY CONTROLLED EXOTHERMIC OXIDATION OF IRON POWDER

[76] Inventor: Katsutsugu Abe, 8-3, Wakabayashi 4-chome, Setagaya-ku, Tokyo, Japan

[21] Appl. No.: 136,695

[22] Filed: Apr. 2, 1980

[30] Foreign Application Priority Data

Apr. 19, 1979 [JP] Japan ................. 54-47226

[51] Int. Cl.³ .................. F24J 1/00; A61F 7/00; F24J 3/00
[52] U.S. Cl. .................. 126/263; 126/201; 44/3 R; 44/3 A; 44/3 C
[58] Field of Search ............. 44/3 R, 3 A, 3 B, 3 C; 126/204, 263

[56] References Cited

U.S. PATENT DOCUMENTS

| | | | |
|---|---|---|---|
| 1,609,958 | 12/1926 | Perrault | 44/3 B |
| 1,819,807 | 8/1931 | Baysinger | 44/3 A |
| 2,573,791 | 11/1951 | Howells | 126/263 |
| 3,976,049 | 8/1976 | Yamashita et al. | 126/263 |
| 4,106,477 | 8/1978 | Feld | 126/204 |
| 4,106,478 | 8/1978 | Higashijama | 44/3 A |
| 4,205,957 | 6/1980 | Fujiwara | 44/3 A |

FOREIGN PATENT DOCUMENTS 1208903 2/1960 France ................. 126/263

Primary Examiner—Gary P. Straub
Attorney, Agent, or Firm—Brisebois & Kruger

[57] ABSTRACT

A warming device in which a mixture of iron powders and metal salts of acids are contained in an inner pouch having gas-permeability and water-permeability, and the inner pouch and a water-carrying member containing water are put in an outer covering body having thermo-regulating holes. The device provides heat by the exothermic reaction caused by oxidizing the iron powder.

5 Claims, 3 Drawing Figures

WARMING DEVICE FOR GENERATING HEAT BY CONTROLLED EXOTHERMIC OXIDATION OF IRON POWDER

BACKGROUND OF THE INVENTION

1. Field of the Invention

The present invention relates to a warming device heated by the exothermic reaction of oxidation of iron powders or iron filings, and more particularly, to such a device which uses a combination of a pouch in which iron powders and acid salts of metals are housed, and a water-carrying body containing water.

2. Brief Description of the Prior Art

Recently developed body warmers are so-called chemical body warmers which generate heat by the oxidizing reaction of iron powder, etc., and which do not have rapid combustion, in comparison with the conventional body warmers which have a combustion mechanism as a heat generator. The chemical body warmer has a container containing a mixture of, mainly, malleable iron, carbon powder, metal salts and water, and covering member which covers the mixture so that air is excluded until the device is used. In use, the container is taken out of the covering member, the substances contained in the container are well shaken and thus air is supplied causing the exothermic reaction.

Although these body warmers are sufficiently convenient ones, the duration of heat generation in an appropriate amount, in case such devices are worn on a person's body is short, and is limited to 20–24 hours at the longest. Furthermore, from the point of view of complete utilization of iron at one-time use, there is the disadvantage that in spite of the existence of substantial amounts of unreacted iron after the use of the device, sufficient temperatures for supplying heat to a body warmer can not be maintained. Therefore, it can be said that such conventional devices have still uneconomical defects in view of the resources and energy conservation required at the present time.

The conventional devices have an advantage that there is no necessity of supplying water at the time of using them. However, since water is contained therein initially and strong generation of heat is created only by supplying air, the manufacturing of those devices should be carried out while excluding contact with air, preferably in an atmosphere of nitrogen.

This is, however, a practically impossible manufacturing method, so that it has been necessary to manufacture them in the air. Therefore, oxidation of the iron powders proceeds and generates heat during the manufacturing of those conventional devices and as a result, energy is wasted. Still further, the conventional devices have the disadvantage that during storage thereof, air gradually penetrates into the inside of the device through the outer cover to cause deterioration of the device, and moisture inside of the device gradually evaporates, so that heat cannot be generated when needed.

SUMMARY OF THE INVENTION

The primary object of the present invention is to provide a warming device which generates heat when water is added.

Another object of the present invention is to provide a warming device in which the duration of heating can be regulated depending on the amount of water contained in a water-carrying member.

Still another object of the present invention is to provide a warming device in which an inner pouch filled with a mixture of iron powder and metal salts of acids is placed against a water-carrying member and the inner pouch and the water-carrying member are then housed in an outer covering having thermoregulating holes to regulate the reaction temperature.

Other objects of the present invention will become more apparent from the brief description and accompanying drawings.

DETAILED DESCRIPTION

Figure 1:
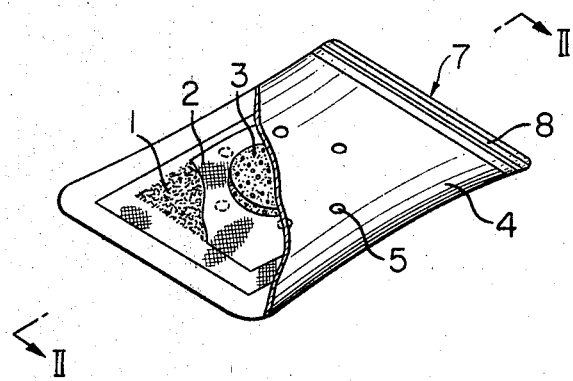
FIG. 1 is a perspective view, partly in section, of a body warmer showing one embodiment of the present invention.
Figure 2:
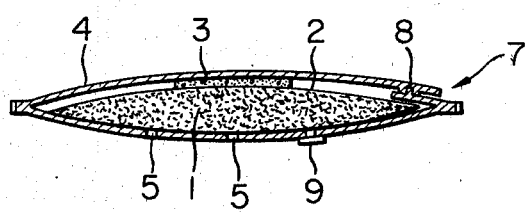
FIG. 2 is an enlarged view taken along the line II—II of FIG. 1.
Figure 3:
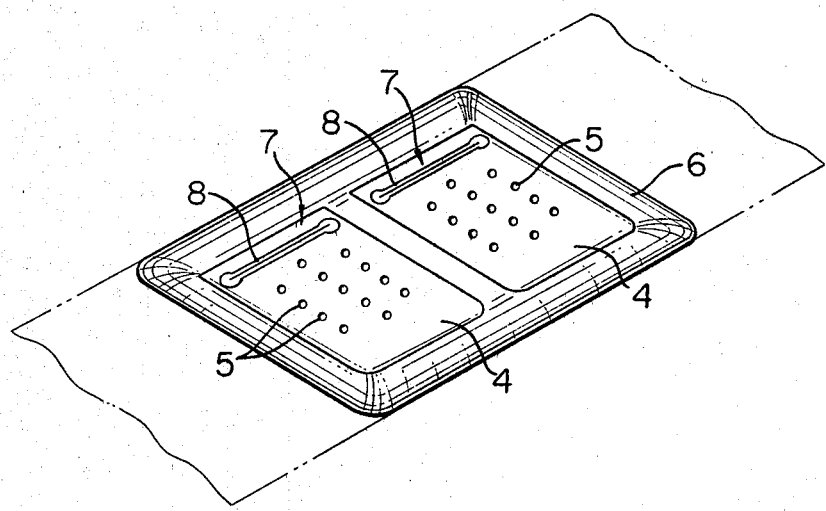
FIG. 3 is a perspective view showing another embodiment of the present invention.

FIGS. 1 and 2 show an embodiment of a warming device of the present invention, used as a body warmer or pocket heater. The present invention consists of a durable inner pouch 2 in which a given amount of a mixture 1 of iron powders or iron filings, and metal salts of acids is housed and sealed, a water-carrying member 3 having hydrous property and flexibility such as a spongy body, filter paper, synthetic resin-foam and the like, and a water-proof material outer cover 4 in which the inner pouch 2 and the water-carrying member 3 are housed with the water-carrying member 3 placed against the inner pouch 2. Thermoregulating holes 5 which are small in size are provided in one wall of the outer cover 4. In this embodiment, the outer cover 4 is a bag, but it may be a pocket provided with a base 6 such as a pad to be attached to a belt, and the like.

In use, a given amount of water is added to the water-carrying member 3, the water-carrying member 3 is placed or stacked on the inner pouch 2, and the water-carrying member and the inner pouch are housed in the outer cover 4. In this case, the water-carrying member 3 faces the inner surface of the wall of the outer cover 4 in which holes are not provided. The water contained in the water-carrying member 3 passes through the material of the inner pouch 2 and further permeates inside of the inner pouch 2 together with the air which enters through the thermoregulating holes 5, whereby iron powders are oxidized and heat is generated.

The outer cover 4 has an opening 7 through which the inner pouch 2 and the water-carrying member 3 are inserted, and which can be sealed by a closure 8 during use of the device. It is most desirable to use an outer cover 4, for example, which has only a small number of holes in only one wall. Cover 4 is of a water-proof material which does not allow the passage of water and it can include the water-carrying member 3 therein on the side of the wall in which the holes are not provided. The warming device of the present invention according to the above-mentioned construction can keep a temperature of 40°–52° C. for about 60 hours, for example, under the condition the 40–50 g of a mixture of iron powders and salts of metals are contained in the pouch, 6–10 ml of water is contained in the water-carrying member 3, and the total area of the thermoregulating holes is 15 mm$^2$.

This is three times the heat generating time of the conventional chemical body warmer. Where the area of the holes is 60 mm$^2$, the temperature remains at 40°–60° C. for about 35 hours. Since the heat generating time is regulated by the amount of the water contained in the water-carrying member 3, divisional use of at least two times or more is possible by adding to the water-carrying member 3 an appropriate amount of water. In this respect, the conventional chemical body warmer can be used only one time. On the other hand, the present invention can be used repeatedly or several times, which is a great advantage of the present invention.

In the present invention, it is preferable to gradually supply the water going into the inner pouch by movement of a person's body or by various forces such as pressure from the outside through a person's clothes and so on. Furthermore, where, for example, one face of the outer cover is provided with holes, it is not desirable to maintain too much water in the outer cover 4, to prevent leakage. However, as mentioned above, when the device is used by supplying water several times, the ideal temperature is possible without soiling clothes. Thus, in comparison with conventional chemical body warmers, the present invention has the further advantage that water is supplied only at the time of use of the device.

As the present invention does not contain water in the mixture at the time of manufacturing, there is no loss of heat generation even if it is manufactured in air at room temperature. Furthermore, exothermic reaction does not occur in the device according to the present invention, until water is added. Therefore, the present invention has excellent stability of the product.

In this respect, the conventional devices are designed to avoid contact with the air until the device is actually used, and it is not expected to completely prevent contact with the air. Moreover, since some shaking and mixing, folding, and slight contact with the air cannot be avoided until the device is delivered to a user, after it is manufactured, these defects have caused inferior goods, insufficient heat generation and so on. However, the warming device of the present invention does not have the above-mentioned defects of the conventional devices.

The present invention is further explained by listing each material for the use in the present invention, but the present invention is not limited to the listed materials because the present invention has as an improvement the initiation of the exothermic reaction by adding water at the time of use of the device. Pure reduced iron which is used in the conventional devices can be used. However, it is most ideal to use sufficiently crushed iron filings of cast iron, pig iron, etc. containing carbon in the iron. Where malleable iron is used and has a 3–4% carbon content, no carbon powder is required to be added. Since pig iron powder is a solid solution with carbon, it is very useful in the present invention.

In other words, in case of addition of carbon powder, only surface reaction of iron is often completed, and reaction inside of the iron is incomplete, so that there is a problem in continuing the reaction. Granular size of the powder is not especially limited, but it is enough to be 100–400 mesh. As salts to be mixed with iron, it is economical to use alkali metals, alkaline earth metals, aluminum and salts of mineral acids, whereby good results can be obtained. Especially, hydrochlorides and nitrates of alkali metals are preferable, and diluted mineral acids and organic acids are also effective for the present invention. The proportion of those substances which are used singly or combined is within ranges of more than 10%, preferably 1–10%, even though the proportion of each of those substances to be used with respect to iron powder is different.

More definite examples are potassium chloride, sodium chloride, potassium nitrate, sodium nitrate, calcium chloride, magnesium chloride, barium chloride, calcium nitrate, magnesium nitrate, magnesium sulfate, ferric sulfate, aluminum chloride, citric acid, malic acid and so on. As the amount of a mixture of both iron powder and salts for one pouch to be used in a body warmer, 40–50 g is appropriate. For the pouch, materials capable of heat-sealing are useful. And materials prepared by impregnating resins into paper, or uneven fabric or paper fabric on which a film made of polyethylene and so on having heat-sealing property and being provided with holes, are laminated, can be used. The outer covering body is a bag, case or pocket for receiving the inner pouch housing the mixture. The outer covering body is a bag made from a cloth prepared from synthetic resin, rubber, etc. into which water is permeable, or a case made of metal or plastics, which has on one face or plural faces, one or plural holes for taking in air. Moreover, it should be one in which the inner pouch can be removed and replaced, and which can be sealed.

The holes 5 are to control temperature. In proportion to the large size of the total area thereof, the temperature becomes greater. Therefore, as shown in FIG. 2, temperature can be controlled by regulating the air entry area by covering a thermoregulating hole 5 with a lid or closure 9.

The thermoregulation is not limited to the above-mentioned form of covering the hole 5 with the lid 9, and any forms which can change the open area of the holes 5 may be applicable, for example, a combination of a slit and a shutter can be used. Furthermore, the present invention is not limited to the case where the holes 5 are positively provided in the outer cover 4. For example, when a zipper, magic fastener and the like are employed for closing the opening, the gap formed between the elements of the zipper, magic fastener and the like can be utilized as the holes for thermoregulation.

In the case of a body warmer, the maximum amount of water to be added is up to about 20% with respect to the contents in the inner pouch. When water more than the critical amount is added, the spaces between the particles of the substances in the inner pouch are filled by water, so that necessary flow of air is prevented and as a result, heat cannot be generated. On the other hand, even when the added amount of water is little, heat generation occurs. However, since the water gradually evaporates due to heat generation, the time of uses becomes shorter with only a little amount of water. The appropriate adding amount is about 15% of the content of the inner pouch.

As the water-carrying member, it is preferable to use a foamed body having great expansion and contraction such as rubber, synthetic resin, cellulose, etc. And it is desirable to use materials which are highly absorbant. Although the exothermic hours at one time of use are different due to the amount of water added and the total area of the holes provided in the outer cover, where the present invention is used as a warmer, it is preferable that the added amount of water is about 15% of the weight of the exothermic materials, and the hole area for taking-in the air is about 15–60 mm$^2$. Under the above-mentioned conditions, the heat generation occurs for 9–18 hours by one addition of water, for 19–30 hours by a second addition of water, and for 6–10 hours by a third addition of water. The addition of water is necessary because the added water gradually evaporates during the heat generation. When water or moisture is exhausted, heat generation ceases. Therefore, more water is required every time the moisture is driven off, but the heat generation substances are normally used up by three water-additions. With the addition of water three times, although there is difference according to the area of the holes for taking in air, heat is generated 40–60 hours at about 55°–60° C. at the highest.

The present invention can be utilized in wide applications as a device such as a body warmer, waist band, foot-warming device, cushion and so on.

The following is an example of the present invention.

EXAMPLE

| | \multicolumn{6}{c}{Name of Element} |
|---|---|---|---|---|---|---|
| | Fe | C | Si | Mn | P | S |
| % | 92.54 | 3.57 | 2.64 | 0.48 | 0.217 | 0.088 |
| Mesh | +150 | ~200 | ~250 | ~325 | −325 | |
| % | 4.8 | 26.1 | 12.6 | 27.7 | 28.8 | |

An inner pouch was prepared in such a manner that 40 g of cast iron powder consisting of the above elements and 2 g of NaCl powder were sealed into a paper pouch impregnated with polyethylene. The thus prepared inner pouch was inserted in an outer cover which was a vinyl bag of 10 cm in width and 12 cm in length, and provided with twelve holes for air entry of 2 mm in diameter on its one side.

At the other side, i.e., the inside face of the cover having no holes, a sponge of synthetic resin containing 7 g of water was placed on the inner pouch within the outer cover and the cover was sealed. With the above-mentioned structure, the substances in the pouch started to generate heat after two minutes. In use, the outer cover containing the inner pouch and the sponge was put in clothes worn by a person and kept generating heat.

Heat was generated for 14 hours until the temperature dropped to 40° C. During this period, the highest temperature was 58° C.

For use a second time, 7.3 g of water was added to the sponge. The highest temperature was 58° C. After 24 hours passed, the temperature dropped to 39° C.

For use a third time, 6.4 g of water was added. In this case, the highest temperature was 57° C. and heat was generated for 9 hours until the temperature dropped to 40° C.

The total duration of the heat generation was 47 hours.

What is claimed is:

1. A heating device for generating heat by an oxidizing reaction caused by contacting iron powder, metal salts of acids, with water and air, to gradually oxidize the iron powder, said device comprising:
   an inner pouch having an air and water permeable wall;
   a quantity of initially dry iron powder and metal salts of acids within said inner pouch;
   means closing said pouch to prevent the escape of the iron filings and metal salts of acids from the pouch;
   an outer covering of waterproof material for containing the inner pouch;
   means for opening and closing an opening in said outer covering to permit insertion into, and removal of said inner pouch from the outer covering;
   an initially dry water absorbing element within said outer covering and engaging said wall of the inner pouch said water absorbing element being selected from the group consisting of, a sponge, synthetic resin-foamed material, or cellulose;
   said outer covering having a plurality of thermoregulating holes formed therein on only one side thereof and said water absorbing element facing toward another side of the outer covering which is free of holes;
   said air and water permeable wall of said inner pouch cooperating with said water absorbing element and the holes in the outer covering to provide means for moistening the iron filings and salts and for allowing the circulation of air, to provide a controlled exothermic reaction, after supplying the water absorbing element with a predetermined quantity of water;
   said water absorbing element moistening said iron powder and salts through the water permeable wall, without excessively wetting said iron powder and salt, so that vapor generated by heat in the pouch can permeate the wall of the pouch together with air to control the generated heat; and wherein
   said water absorbing member comprises means for allowing the user, when heat is to be generated, to add to the device a predetermined quantity of water less than that required for complete oxidation of the iron powder, by wetting the moisture absorbing element, so that the device can be reused by later adding more water to the water absorbing element.

2. The device as claimed in claim 1, wherein the outer covering comprises a bag.

3. The device as claimed in claim 1, wherein the outer covering comprises a pocket attached to a pad or base of other materials.

4. The device as claimed in claim 1, further comprising means for selectively opening or closing said holes.

5. The device as claimed in claim 1, wherein the water absorbent member is selected from the group consisting of, a sponge, filter paper or synthetic resin-foamed material having flexibility and water-absorbability, and heat generation time is regulated by the size and water absorbency of the water absorbent member.

* * * * *